(12) United States Patent
Eberle et al.

(10) Patent No.: US 10,272,438 B2
(45) Date of Patent: Apr. 30, 2019

(54) DEVICE FOR RECEIVING AND STORING CONTAINERS

(71) Applicant: ANDREAS HETTICH GMBH & CO. KG, Tuttlingen (DE)

(72) Inventors: Klaus-Guenter Eberle, Tuttlingen (DE); Natascha Schaldecker, Tuttlingen (DE)

(73) Assignee: ANDREAS HETTICH GMBH & CO. KG, Tuttlingen (DE)

( * ) Notice: Subject to any disclaimer, the term of this patent is extended or adjusted under 35 U.S.C. 154(b) by 0 days.

(21) Appl. No.: 15/126,283

(22) PCT Filed: Mar. 17, 2015

(86) PCT No.: PCT/EP2015/055588
§ 371 (c)(1),
(2) Date: Sep. 14, 2016

(87) PCT Pub. No.: WO2015/140187
PCT Pub. Date: Sep. 24, 2015

(65) Prior Publication Data
US 2017/0080431 A1   Mar. 23, 2017

(30) Foreign Application Priority Data
Mar. 21, 2014 (DE) ........................ 10 2014 103 930

(51) Int. Cl.
*B01L 9/06* (2006.01)
*C12M 1/24* (2006.01)
*C12M 3/00* (2006.01)

(52) U.S. Cl.
CPC .............. *B01L 9/06* (2013.01); *C12M 23/08* (2013.01); *C12M 23/48* (2013.01); *B01L 2300/0848* (2013.01)

(58) Field of Classification Search
None
See application file for complete search history.

(56) References Cited

U.S. PATENT DOCUMENTS 2,568,405 A   9/1951   O'Malley
3,199,684 A   8/1965   Bradley
(Continued)

FOREIGN PATENT DOCUMENTS

DE   1881774   10/1963
DE   7224740   10/1972
(Continued)

OTHER PUBLICATIONS

The International Bureau of WIPO, PCT International Preliminary Report on Patentability, dated Sep. 21, 2016, p. 1-11, International Application No. PCT/EP2015/055588, Applicant: Andreas Hettich GmbH & Co. KG.
(Continued)

*Primary Examiner* — Paul S Hyun
(74) *Attorney, Agent, or Firm* — Woodling, Krost and Rust

(57) ABSTRACT

The invention relates to a device (10) for receiving and storing containers (12), in particular test tubes. The device has at least one support bar (22) with recesses (26), a front face (16) and a standing strip (20) arranged opposite the front face (16). One recess (26) in the support bar (22) is assigned to each container (12), the support bar being used as the first support. The standing strip (20) receives the base of the container (12) and axially secures the container (12). The invention is characterized in that a folding mechanism (40) is provided for at least two folding positions, which mechanism orients the device lying on a standing surface (14) into a first folding position at a first angle ($\alpha$) to the
(Continued)

standing surface (14) and a second folding position at a second angle ($\beta$) to the standing surface (14).

13 Claims, 2 Drawing Sheets

(56) References Cited

U.S. PATENT DOCUMENTS

| | | |
|---|---|---|
| 4,407,958 A | 10/1983 | Degraff |
| 5,150,784 A | 9/1992 | Keine |
| 2009/0101539 A1 | 4/2009 | Qian et al. |

FOREIGN PATENT DOCUMENTS

| | | |
|---|---|---|
| EP | 1442674 A1 | 4/2004 |
| EP | 1442674 | 8/2004 |

OTHER PUBLICATIONS

PCT/EP2015/055588 International Search Report and Writtent Opinion, dated June 9, 2015, 12 Pages.

DEVICE FOR RECEIVING AND STORING CONTAINERS

This patent application is the national phase entry of PCT/EP2015/055588. PCT/EP2015/055588, international application filing date Mar. 17, 2015, claims the benefit and priority of and to German patent application no. DE No. 10 2014 103 930.0, filed Mar. 21, 2014. PCT/EP2015/055588, international application filing date Mar. 17, 2015 and German patent application no. DE No. 10 2014 103 930.0, filed Mar. 21, 2014 are incorporated herein by reference hereto in their entireties.

The invention relates to a device for receiving and storing containers, in particular test tubes.

For culturing certain microorganisms, solid nutrient media are used which usually contain agar-agar (also called agar) as a solidifying ingredient. The culture medium is prepared by mixing the agar, which is in powder form, as well any other ingredients with hot water. The culture medium will then solidify during cooling.

Although Petri dishes are also used for growing microorganisms, test tubes are sometimes preferred, amongst other things because they can be stored in a more space-saving manner and can be closed more easily, and the risk of spilling is lower. However, the surface of the medium is obviously small in vertically positioned test tubes. In order to obtain a larger surface, the test tubes are usually arranged in a slanted position, in particular during the cooling and solidifying phases. Culture media produced in this manner are also referred to as agar slant. Depending on the intended use, different angles are preferred for this purpose, frequently 5° or 20° to the standing surface, said angle relating to the longitudinal axis of the test tube storing the agar slant with respect to the standing surface of the test tube, i.e. relating to the support axis defined by the supports which determines the orientation of the introduced container. In the case of a cylindrical container, the support axis and the longitudinal axis of the container are parallel to each other.

U.S. Pat. No. 4,407,958 proposes a rack in which test tubes can be stored both vertically and at the above mentioned angles of 5° and 20°. The rack essentially consists of a rectangular base plate, two support plates of the same size disposed in parallel above it, and two connection plates which space said carrier and support plates from each other along their widths and in the vertical dimension and connect them via lateral connection plates. The base plate and the support plates have a multitude of apertures which are aligned with respect to each other and dimensioned such that the bottom end of a test tube can be inserted through a first aperture in the upper support plate and an associated second aperture in the second carrier plate until the bottom end of the test tube is finally received in a third aperture in the carrier plate which is smaller than the test tube and which axially secures the test tube. The connection plates are each subdivided into two plate areas which are connected to each other via a web and form a roughly V-shaped aperture which is open toward the bottom. The two plate areas each have inner edges which face each other and are inclined toward each other. The lower edges of the two plate areas are positioned in parallel to the standing surface and in parallel to the base and support plates and each form a foot for the standing surface of the rack. The connection plates run perpendicular to the base and support plates. The outer edges of the connection plates are inclined by 5° and/or 20°, resp., with respect to the vertical extension of the rack so that the connection plates increase in width from the bottom to the top, i.e. by 5° on the first longitudinal side of the rack and by 20° on the second longitudinal side of the rack.

For storing the test tubes in a vertical position, the rack stands on the lower edges of the connection plates. For storing the test tubes in a slanted position, the rack is tilted on one of its longitudinal sides so that it is supported on the outer edges of the connection plates. The choice of the longitudinal side thus determines the angle at which the test tubes are positioned.

The reliable alignment and storage at the exact angle desired and the relatively uncomplicated selection of the angle are indeed advantageous here. However, one of the disadvantages of this solution is the size of rack. Viewed from the starting position for positioning the test tubes vertically, the height of the construction is predetermined by the length of the test tubes, and a certain minimum width is required for the stability of the construction. This proves particularly disadvantageous when the rack is used in small incubators. Moreover, cleaning might be difficult since the rack may be too large to be cleaned in small autoclaves, and even a manual cleaning process will not reach all the spots. Furthermore, handling of the rack is difficult, not least so because of its size, since changing the positioning angle requires the rack to be completely realigned. This is quite cumbersome, especially when space is limited, like in an incubator.

It is the object of the invention to provide a device for inserting containers, in particular test tubes, which avoids the above mentioned shortcomings, is of a space-saving design and can be cleaned easily.

The invention is based on the finding that for the slanted positioning of containers, in particular test tubes, a small rotary movement of the rack by the desired angle will suffice, and that this rotary movement can be ensured by an adjusting mechanism. A mechanism for adjusting the positioning angle may be constituted in a simple manner by a folding mechanism.

According to the invention, the device for receiving and storing containers, in particular test tubes, comprises at least one support bar with recesses formed therein, each recess in the support bar being assigned to one container and serving as a support. Furthermore, a front face and a standing strip arranged opposite said front face are provided. The standing strip is used to support the base of the container and to axially secure the container in this position. The distance between the support bar and the standing strip has been chosen such that test tubes of all lengths available on the market can be stably supported in the device. Preferably, a folding mechanism having at least two folding positions is provided, which, in a first folding position, will align the device resting on a standing surface at a first angle to the standing surface and, in a second folding position, will align the device at a second angle to the standing surface. So, with minimum effort, the most suitable angle can be selected from among the angles most frequently used in the respective field for storing microorganisms, and the device can then be positioned at this angle. The angle is defined between the longitudinal axis of the test tube received and stored in the device and the standing surface of the device and thus relates to the positioning of the support with respect to the contact surface for the container.

According to one aspect of the invention, a base plate, a first support and a second support are provided for one container each, with the supports being more specifically spaced from each other and serving to position the container at a third angle relative to the base plate. The two spaced supports ensure more reliable support. Moreover, the third angle can be chosen to be equivalent to an angle frequently used in the respective field of application for storing containers, so that once the container has been placed on the support, no further angle adjustment will be required.

It is advantageous for the standing strip to comprise second supports, or for a second standing strip to be provided which comprises second supports. Where second supports are provided in the standing strip, this will guarantee secure support of the containers without requiring any additional component—which simplifies the design of the device and saves costs. However, it may also prove advantageous to have a second strip in place. In this case, the standing strip can be manufactured more easily, and the support point of the containers on the second standing strip is spaced from the container base, making for an even more reliable support.

According to one embodiment of the invention, it has proven advantageous to choose the first angle at 5° and the second angle at 20°. In this case, the containers will be supported in parallel to the base plate, i.e. the longitudinal axis of the containers will be parallel to the base plate, and the folding mechanism is then used to select one of the two angles 5° and 20° to the standing surface, i.e. the folding mechanism of the device is used to position the supports for the containers in such a way that one of the above angles is defined between the longitudinal axis of the containers received in the device and the standing surface of the device. As culture media with aerobic cultures are typically stored at an angle of 5° and culture media with anaerobic cultures are typically stored at an angle of 20°, this option fulfils frequent practical requirements.

In an advantageous embodiment of the invention, the support bars and standing strips are arranged in parallel to a longitudinal axis of the device. This facilitates the production of the device and ensures safe storage and support of the containers.

It is considered advantageous to provide the supports in a U-shaped design open to the top and adapted to the container. In particular, it is favourable here to have a cross-section of the support which gradually widens from the bottom to the top in such a way that test tubes of all diameters available on the market can be stably supported and stored in the device. As a result, the containers can be received more easily and they will be even more reliably supported in the device.

For an as easy as possible operation and an as stable as possible design of the folding mechanism, it comprises a stop bar which corresponds in length to the base plate, as well as two mounting tabs which are provided perpendicularly at either end of the stop bar. The mounting tabs on either front face of the device thus support the stop bar in such a way that it can be folded about a rotary axis which is parallel to the longitudinal axis. The support angle may thus be set quite simply by suitably positioning the stop bar. The fact that the length of the stop bar extends along the entire length of the base plate makes the folding mechanism extremely stable.

In an alternative embodiment, the stop bar comprises at least two feet. More specifically, these feet are integrally formed with the stop bar and made of the same material and, in the first folding position, the feet and the stop bar form a flat support surface. As a result, a narrower design is possible for the stop bar—which saves material and reduces weight. Positioning the feet conveniently, in particular at the two ends of the stop bar, will safeguard the high level of stability of the construction.

Preferably, the mounting tabs are each attached to a wall part via a rotary joint which is provided on the two front faces and mounted in perpendicular alignment to the base plate. This allows the folding mechanism to be mounted on the device in a simple and stable manner, which reduces material costs and construction effort.

Furthermore, it has proven advantageous, in the first folded position, to have the feet of stop bar abut on the underside of the base plate and, in the second folded position, to have the stop bar abut on a support bar, with the feet resting on the standing surface. The design of the stop bar, essentially its thickness and height, thus determines the first and second angles, and the fact that the stop bar, over its entire length, abuts on either the base plate or a support bar ensures optimum stability.

It is particularly advantageous to choose equal dimensions for the support bars. This facilitates both the production of the device and its assembly, for example after cleaning.

In an advantageous embodiment of the invention, handles are mounted on the front faces. This facilitates transport of the device.

In another advantageous embodiment, the handles are spaced at such a distance from the base plate that they will be located above the support bar, in particular at a distance which is larger than the radius of the U-shaped recess which forms the support. This first of all makes for more reliable handling and transport of the device since the centre of gravity of the device is below the handles. Secondly, this makes it easier to design the handles such that structurally identical devices can be snapped into engagement with them and thus be supported on them.

According to one aspect of the invention, the device is of a design which can be autoclaved, more specifically of a stainless steel design. The resulting device will thus be scratch-proof and abrasion-resistant, acid- and base-resistant, rust-proof and temperature-resistant, and can be cleaned efficiently.

Additional advantages, features and possible applications of the present invention can be gathered from the description which follows, in which reference is made to the embodiments illustrated in the drawings.

Throughout the description, the claims and the drawings, those terms and associated reference signs are used as are listed in the List of Reference Signs which follows below. In the drawings:

Figure 1:
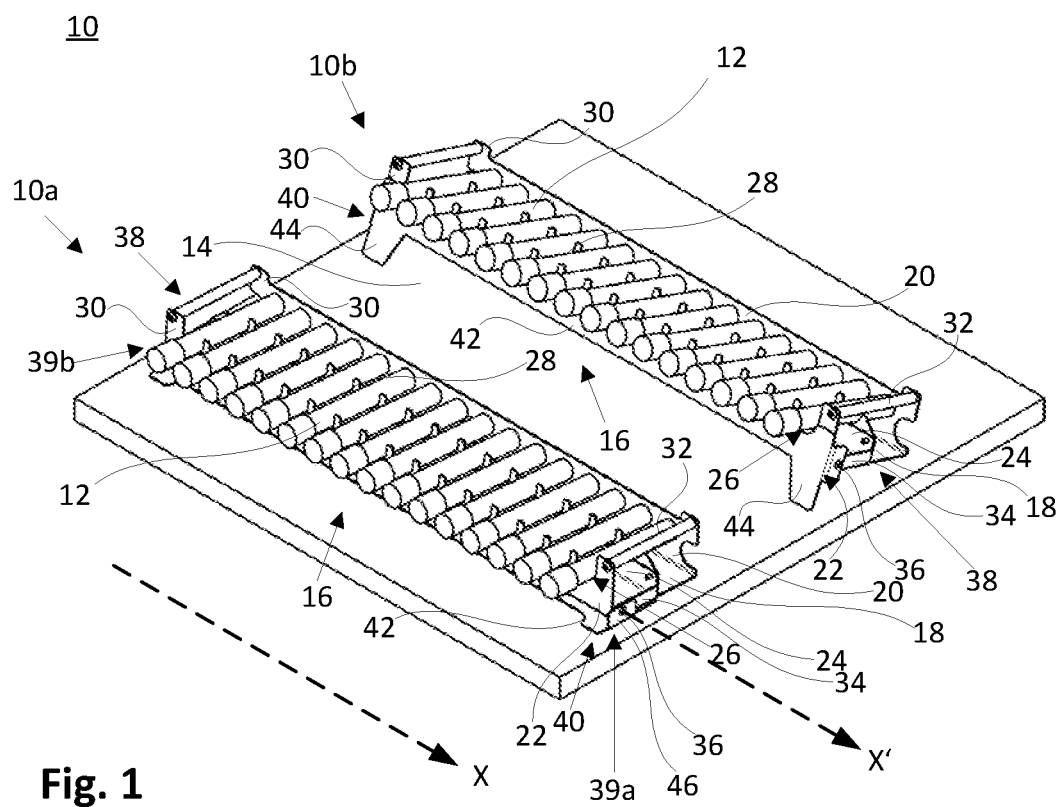
FIG. 1 is a perspective top view of an embodiment of a device according to the invention for receiving and storing containers.

FIG. 1 is a perspective top view of two storing devices 10 according to the invention set up in parallel to each other and holding test tubes 12. The only difference between them is that owing to the respective chosen position of the folding mechanism 40, the front storing device 10*a* is inclined at a smaller angle to the standing surface 14 than the storing device 10*b* behind it, i.e. in the storing device 10, the supports for the test tubes 12 are positioned in such a way that the longitudinal axis of the test tubes 12 introduced into the storing device 10 will take the above mentioned angles to the standing surface 14 of the storing device 10.

Both storing devices 10 each have a front face 16 and a base plate 18, with a first support bar 22, a standing strip 20 positioned opposite said front face 16, and a second support bar 24 disposed between the first support bar 22 and the standing strip 20 being mounted perpendicularly on the front face 16. The bases of the stored test tubes 12 abut on the standing strip 20 and are axially fixed in position by the latter. Furthermore, allocated to the test tubes 12 are recesses 26 in the first support bar 22 and recesses 28 in the second support bar 24. The recesses 26 and 28 are U-shaped and open toward the top and secure the test tubes 12 with respect to a longitudinal axis x of the storing device 10. Provided at both ends 39a and 39b of both the standing strip 20 and the first support bar 22 are raised portions 30 which vertically project the radius of the recesses 26 and 28. Two raised portions 30 each which are positioned opposite each other along the longitudinal axis x are interconnected by a strut which serves as a handle 32.

Provided perpendicular to the base plate 18 on first and second side faces 38, 38 of the storing devices 10, between the first support bar 22 and the second support bar 24 are wall parts 34 which each have a rotary joint 36 on which a folding mechanism 40 is mounted for rotation about a rotary axis x' which is parallel to the longitudinal axis x. The folding mechanism 40 has a stop bar 42 which is of the same length as the base plate 18 and which has two feet 44 integrally formed on its ends 39a and 39b, as well as two mounting tabs 46. The mounting tabs 46 are each mounted in perpendicular to the front-face ends 39a, 39b of the stop bar 42 and are firmly attached to the rotary joints 36.

The storing device 10a has its stop bar 42 folded back under the base plate 18 so that the test tubes 12 are inclined at a first angle α to the standing surface 14. The storing device 10b has its stop bar 42 folded out, with its feet 44 standing on the standing surface 14. This results in a larger second angle β at which the test tubes 12 are inclined to the standing surface 14. For reasons of clarity, angles α and β are shown in FIG. 2.

Figure 2:
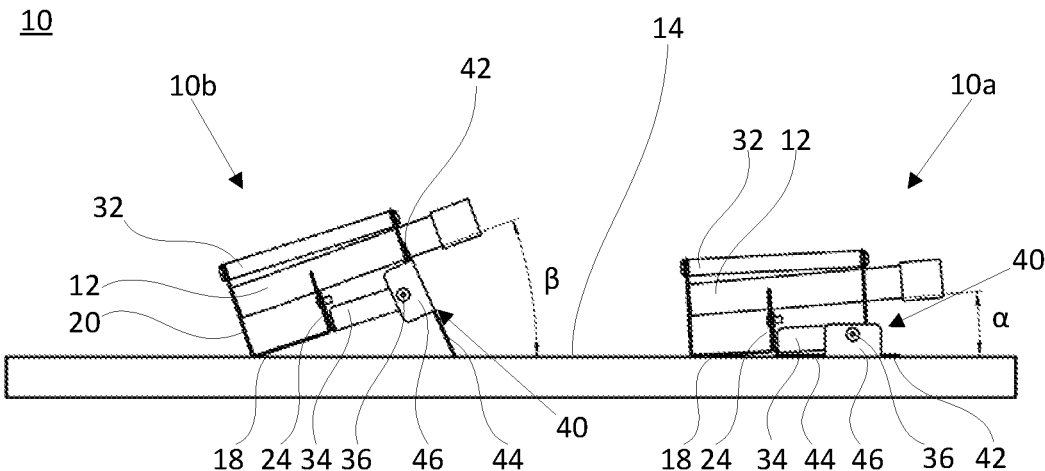
FIG. 2 is a lateral view of an embodiment of FIG. 1.

FIG. 2 is a lateral view of the storing devices 10a and 10b of FIG. 1. As described above, the essentially cylindrical test tubes 12 are supported in recesses 26 provided in the second support bar 22 and in recesses 28 provided in the second support bar 24. Once the test tubes 12 have been inserted in each of the storing devices 10a and 10b, the recesses 26 and 28 will be connected to each other by the inserted test tube 12. A support axis L of the two recesses 26 and 28 extends in parallel to the longitudinal axis of the inserted test tube 12. Defined between the support axis L of the two recesses, but also the longitudinal axis of the inserted test tube 12, and the standing surface each are the angles mentioned above and below.

The storing device 10a has its folding mechanism 40 folded back under the base plate 18 via its rotary joints 36 connected to its mounting tabs 46, with its feet 44 and the stop bar 42 abutting on the standing surface 14. The dimensions of the mounting tabs 46 and the distance of the rotary joints 36 from the base plate 16 have been chosen such that the test tubes 12 will be inclined at a first angle α of 5° to the standing surface 14.

The storing device 10b has its folding mechanism 40 folded out, with its feet 44 standing on the standing surface 14 and the stop bar 42 abutting on the first support bar 22. In this folding position of the folding mechanism 40, the test tubes 12 are inclined at a second angle β of 20° to the standing surface 14.

Angles α and β can either be defined solely by the dimensions and the arrangement of the folding mechanism 40, if the distances of the deepest points of recesses 26 and recesses 28 from the base plate 18 are identical, and the test tubes 12 are thus supported in parallel to the base plate 18. Or the test tubes 12 can be inclined at a certain angle to the base plate 18 by different distances of the deepest points of recesses 26 and recesses 28 from the base plate 18, which angle is then considered for determining the dimensions and the arrangement of the folding mechanism 40.

Figure 3:
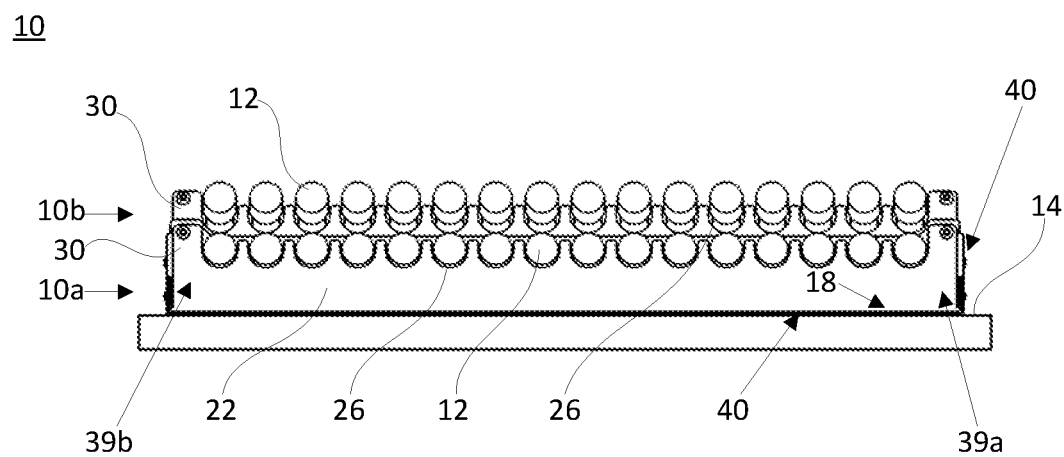
FIG. 3 is a front view of the embodiment of FIG. 1.

FIG. 3 is a front view of the storing devices 10. This perspective clearly shows the difference between angle α at which the test tubes 12 are supported in the storing device 10a, and angle β at which the test tubes 12 are supported in the storing device 10b. The storing device 10a has its folding mechanism 40 folded back under the base plate 18, and the first support bar 22 is completely visible at the front face 16. The test tubes 12 are supported in recesses 26. Formed on both ends 39a and 39b of the first support bar 22 are raised portions 30 which are connected to ends 39a and 39b (not shown) of the support bar 20 via handles 32 not visible in this perspective. However, owing to the larger angle β at which storing device 10b is inclined, it can be seen how the test tubes 12 are also supported in recesses 26 therein.

LIST OF REFERENCE SIGNS 10 storing device
12 test tubes
14 standing surface
16 front face
18 base plate
20 standing strip
22 first support bar
24 second support bar
26 recesses
28 recesses
30 raised portions
32 handles
34 wall parts
36 rotary joints
38 first and second side faces
39 ends
40 folding mechanism
42 stop bar
44 feet
46 mounting tabs
α first angle
β second angle

What is claimed is:

1. A device (10) for receiving and storing containers (12) in combination with a standing surface, comprising:
 a longitudinal axis (x);
 a first support bar (22);
 said first support bar (22) includes recesses (26) in which said containers reside;
 said first support bar (22) supports said containers (12) when said containers are stored;
 a front face (16);
 a standing strip (20) arranged opposite said front face (16) for receiving bases of said containers (12) and for axially securing said containers (12);
 a folding mechanism (40);
 said folding mechanism includes at least two folding positions;
 said folding mechanism includes a rotary axis (x') which is parallel to said longitudinal axis (x);
 said folding mechanism (40) includes a stop bar (42);
 said stop bar (42) has at least two feet (44) integrally formed therewith, said stop bar (42) and said feet (44) are rotatable with respect to said rotary axis (x'), and said feet (44) engaging said standing surface (14);
 said folding mechanism has a first folding position orienting said containers at a first angle (α) with respect to said standing surface (14); and, said folding mechanism has a second folding position orienting said containers at a second angle (β) with respect to said standing surface (14).

2. The device for receiving and storing containers (12) in combination with a standing surface, as claimed in claim 1, further comprising:
   a base plate (18);
   a second support bar (24) supporting said containers;
   said second support bar (24) include recesses (28);
   said recesses (26) of said first support bar (22) and said recesses (28) of said second support bar (24) support said containers (12) when stored; and,
   said recesses (26) of said first support bar (22) and said recesses of said second support bar (24) are spaced from each other and orient said containers (12) when stored at a third angle with respect to said base plate (18).

3. The device for receiving and storing containers (12) in combination with a standing surface as claimed in claim 2, wherein: said first and second support bars (22, 24) and said standing strip (20) are arranged in parallel to said longitudinal axis (x).

4. The device for receiving and storing containers (12) in combination with a standing surface as claimed in claim 2, wherein: said device for receiving and storing containers (12) in combination with a standing surface includes a top portion; and, said recesses (26, 28) of said support bars (22, 24) are U-shaped and open toward said top portion.

5. The device for receiving and storing containers (12) in combination with a standing surface as claimed in claim 2, wherein:
   said base plate has a length;
   said stop bar (42) includes a length and said length of said stop bar corresponds to said length of said base plate (18);
   two mounting tabs (46) are perpendicularly mounted on either end (39a, b) of said stop bar (42);
   said stop bar (42) is attached to a first side face (38) and a second side face (38) via said mounting tabs (46, 46); and,
   said stop bar (42) is rotatable about said rotary axis (x') which is parallel to said longitudinal axis (x).

6. The device for receiving and storing containers (12) in combination with a standing surface as claimed in claim 5, wherein:
   said at least two feet (44) of said stop bar is of the same material as said stop bar (42); and,
   when said folding mechanism is in said first folding position, said feet (44) and said stop bar form a flat support surface.

7. The device for receiving and storing containers (12) in combination with a standing surface as claimed in claim 6, wherein:
   said base plate includes an underside; and,
   when said folding mechanism is in said first folding position, said feet (44) of said stop bar (42) abut on said underside of said base plate (18) and that, when said folding mechanism is in said second folding position, said stop bar (42) abuts on said first support bar (22), with said feet (44) being supported on said standing surface (14).

8. The device for receiving and storing containers (12) in combination with a standing surface as claimed in claim 5, further comprising:
   a wall portion (34); wherein
   each of said mounting tabs (46) is additionally attached to said wall portion via a rotary joint on said front face; and,
   each of said mounting tabs (46) is arranged so as to be perpendicular to said base plate (18) when said folding mechanism is in said second folding position orienting said containers at a second angle (β) with respect to said standing surface (14).

9. The device for receiving and storing containers (12) in combination with a standing surface as claimed in claim 5, wherein: handles (32) are provided on said side faces (38, 38).

10. The device for receiving and storing containers (12) in combination with a standing surface as claimed in claim 9, wherein:
    said handles (32) are arranged at a distance from said base plate (18);
    said handles are located above said support bars (22, 24) at a distance above said support bars (22, 24);
    said first support bar (22) has U-shaped recesses (26) and said second support bar (24) has U-shaped recesses (28); and,
    said distance above said support bars is larger than the radius of the U-shaped recesses (26, 28) of said first and second support bars (22, 24).

11. The device for receiving and storing containers (12) in combination with a standing surface as claimed in claim 2, wherein: said support bars (22, 24) are of identical dimensions.

12. The device for receiving and storing containers (12) in combination with a standing surface as claimed in claim 1, wherein: said first angle is 5° and said second angle is 20°.

13. The device for receiving and storing containers (12) in combination with a standing surface as claimed in claim 1, wherein:
    all of the structure is made of stainless steel.

* * * * *